(12) United States Patent
Donaldson

(10) Patent No.: US 6,764,459 B1
(45) Date of Patent: Jul. 20, 2004

(54) EYE PROTECTOR

(76) Inventor: William Blair MacGregor Donaldson, 45 Carlton Place, Aberdeen (GB), AB15 4BR ( * ) Notice: Subject to any disclaimer, the term of this patent is extended or adjusted under 35 U.S.C. 154(b) by 0 days.

(21) Appl. No.: 09/787,258

(22) PCT Filed: Sep. 3, 1999

(86) PCT No.: PCT/GB99/02908

§ 371 (c)(1),
(2), (4) Date: Oct. 1, 2001

(87) PCT Pub. No.: WO00/13631

PCT Pub. Date: Mar. 16, 2000

(30) Foreign Application Priority Data

Sep. 3, 1998 (GB) .............................. 9819257

(51) Int. Cl.[7] .............................. A61F 13/12; A61F 9/00
(52) U.S. Cl. ......................................... 602/74; 128/858
(58) Field of Search .............................. 602/74, 41, 43, 602/53, 54, 58, 60, 61, 78; 128/858, 206.23, 857; 604/304, 307, 308

(56) References Cited

U.S. PATENT DOCUMENTS

| 3,039,461 A | * | 6/1962 | Hawie | 602/78 |
|---|---|---|---|---|
| 3,068,863 A | | 12/1962 | Bowman | |
| 3,300,786 A | | 1/1967 | Rosenvold et al. | |
| 4,134,401 A | | 1/1979 | Galician | |
| 4,411,263 A | * | 10/1983 | Cook | 128/858 |
| 4,502,476 A | * | 3/1985 | Welt | 128/858 |
| 4,517,972 A | * | 5/1985 | Finch, Jr. | 602/2 |
| 4,549,539 A | | 10/1985 | Donaldson | |
| 4,709,695 A | | 12/1987 | Kohn et al. | |
| 5,295,950 A | | 3/1994 | Godley | |
| 5,769,806 A | | 6/1998 | Radow | |
| 5,817,039 A | * | 10/1998 | Raunig | 602/5 |
| 5,887,590 A | * | 3/1999 | Price | 128/858 |
| 6,034,292 A | * | 3/2000 | Mazaheri | 602/41 |
| 6,293,281 B1 | * | 9/2001 | Shultz et al. | 128/888 |

FOREIGN PATENT DOCUMENTS

DE   35 39 533   5/1987

* cited by examiner

Primary Examiner—Nicholas D. Lucchesi
Assistant Examiner—Fenn C Mathew
(74) Attorney, Agent, or Firm—Lawrence E. Laubscher, Jr.

(57) ABSTRACT

The present invention concerns an eye protector comprising first and second elements intended for attachment respectively to a patient's upper eye lid and to a region of the patient's cheek beneath the ye, and fastener means for releasably fastening the elements together; said fastener means being configured to resist release in response to natural eye lid motion but to release more readily when pulled apart for detachment.

15 Claims, 2 Drawing Sheets

EYE PROTECTOR

This invention relates to eye protectors and it relates more especially to eye protectors of the kind in which an eyelid may be held closed by a releasable means.

Such eye protectors are disclosed in my U.S. Pat. No. 4,549,539, and comprise first and second elements for attachment respectively to an upper eye lid and to a part of the cheek beneath the eye. The two elements are capable of repeated attachment to, and detachment from, one another, and they are arranged so that the eye can be held comfortably in a closed position when the two elements are attached to one another, but can temporarily be allowed to open, for example to permit treatment to be administered, by detaching the two elements from one another.

The respective attachment of the two elements to the eye lid and to the cheek is effected by hypoallergenic adhesive, and the releasable attachment between the two elements may be effected by means such as a cooperative stud and tab, or by the provision, on facing surfaces of the two elements intended in use to overlap, of a material configured to comprise large numbers of hooks and eyes, such as that sold under the Trade Mark VELCRO. In practice, and in commerce, it has been preferred to use the latter technique but in any event it is arranged that the two elements, once having been detached to allow opening of the eye, can be reattached in substantially the same relative disposition as they adopted when the eye was originally closed.

These protectors have found market acceptance, but exhibit a problem in that, when detaching the two elements from one another, it is possible for the lower element to become detached from the cheek by the force used to separate the two elements, or at least to so weaken the lower element's attachment to the cheek that normal eyelid movements may pull the lower element from the cheek. The principal problem caused by detachment of the lower element from the patient's cheek is that it is difficult to re-attach the lower element in a satisfactory manner. As a result, a complete new eye protector is required. Moreover, any failure of the eye protector to hold the patient's eye shut clearly can also be dangerous to the wearer since the eye is not properly protected. Furthermore, such failure involves wastage of materials and means that the eye area will have to be prepared again to receive the new lower element. Such preparation can involve pain, or at least discomfort, associated with the cleaning of potentially highly sensitive regions close to the patient's eye.

It is an object of this invention to address the above problems.

According to the present invention, there is provided an eye protector comprising first and second elements intended for attachment respectively to a patient's upper eye lid and to a region of the patient's cheek beneath the eye, and fastener means for releasably fastening the elements together; said fastener means being configured to resist release in response to natural eye lid motion but to release more readily when manually pulled apart for detachment. Such an arrangement provides an eye protector which is less likely to fail by detachment of the second element on attempted unfastening of the first element therefrom.

Preferably, said fastener means comprises co-operatively retentive material carried by surfaces of respective components forming part at least of each of said first and second elements and intended in use to assume an overlying and contacting relationship. Such material may be of the type available under the Trade Mark VELCRO which exhibits particular advantages in its flexibility in position of attachment.

Most preferably, the first element is provided with a strip-like dependent portion extending downwardly, across the patient's eye, and bearing said retentive means configured to overlie co-operative retentive means carried by the second element, the arrangement being such that the area of overlap between the retentive means borne by said strip-like portion and that carried by the second element is relatively small compared with the area of the second element as affixed to the patient's cheek.

In a particularly favoured arrangement, the second element carries a strip of said retentive material, said strip extending, in use, substantially orthogonally to the said strip-like portion depending from said first element.

Conveniently, though not of course necessarily, the said element intended for attachment to the patient's upper eye lid comprises a tab portion not provided with retentive material and intended to be manipulated to detach the two elements from one another. The provision of such a tab portion not provided with retentive material enhances the ease of unfastening the first and second elements, since the tab portion is thereby discouraged from fastening itself in an orientation in the direction of natural eye lid motion. The tab portion may be formed to have a memory for orientating itself away from the eye in use.

In other embodiments of the invention, which may be used alternatively to or in combination with the preferred embodiment described above, the retentive material carried by at least one of said overlying components conforms to a pattern which presents a relatively wide profile facing the patient's eye and a profile of reduced width facing said tab portion. As such, the first and second elements will more readily separate when pulled apart manually from the tab portion. Said pattern may link said relatively wide profile to said profile of reduced width by means of at least one substantially linear slant or by means of at least one outline conforming to one of an exponential, logarithmic or sinusoidal form.

Conveniently, either or both of said first and second elements includes a component shaped to present a wider profile towards the patient's eye than away therefrom.

The second element (that intended for attachment to the patient's cheek) may conveniently be configured for attachment to an area overlapping the lower part of the eye socket of the patient. In this manner, the element intended for attachment to the patient's cheek can be securely anchored near the lower part of the patient's eye socket.

The retentive means provided on the second element is preferably carried only on a portion thereof. In this regard, such retentive means provided to the second element conveniently extends only to an area intended to be affixed near the lower edge of the patient's eye socket and does not overlap the same when attached thereto in use. The second element may be provided with alignment means to facilitate its attachment to the patient's cheek, namely it may be marked or shaped so that the fastener means provided thereto can be readily aligned with the lower edge of the eye socket. As such, the attachment of the second element to the patient's cheek is enhanced to resist separation on detachment of the fastener means.

With such an arrangement, the tab portion on the first element tends to be orientated at least partially out of the direction of natural eye lid motion, thereby enhancing the ease of detachment of the fastener means.

According to a second aspect of the present invention there is provided an eye protector comprising first and second elements intended for attachment respectively to a patient's upper eye lid and to a region of the patient's cheek beneath the eye, and fastener means for releasably fastening the elements together; wherein said first element is provided with a strip-like dependent portion extending downwardly, and bearing VELCRO (trade mark) retentive means configured to overlie co-operative VELCRO (trade mark) retentive means carried by the second element, the arrangement being such that the ratio of the area of the second element as affixed to the patient's cheek and the area of overlap between the retentive means borne by said strip-like portion and that carried by the second element is in excess of 2.5:1.

In order that the invention may be clearly understood and readily carried into effect, some embodiments thereof will now be described, by way of example only, with reference to the accompanying drawings, of which:

Figure 1:
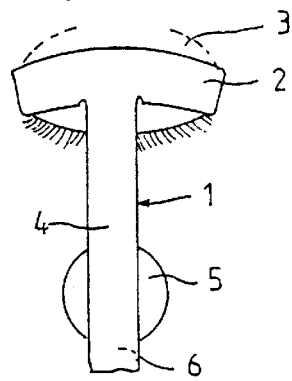
FIGS. 1 and 2 show, in plan and profile views respectively, an eye protector of the general kind described above.
Figure 2:
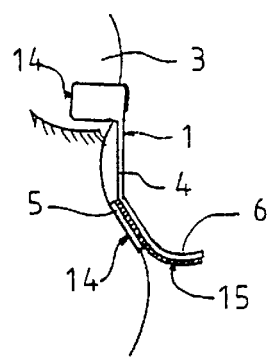

Referring to FIGS. 1 and 2, an eye protector of the general kind described above comprises a first element 1, having a portion 2 attached by means of hypoallergenic adhesive 14 to the upper lid 3 of a patient's eye, and a portion 4 depending downwards from the portion 2, the element 1 being effectively "T-shaped". A second element 5 is similarly attached to the cheek of the patient, below the eye.

The inner surface of the dependant portion 4 of the element 1 (i.e. that surface which, in use, will face the cheek of the patient) is provided, over at least a part of its length close to its end remote from the portion 2, with a component of a releasable attachment means such as an area 15 of the material sold under the Trade Mark VELCRO; the outwardly facing surface of the second element 5 being provided with a co-operative component of the attachment means, in this example another area of VELCRO material. The portion 4 has a continuation portion, forming a tab 6 which is intended to be pulled to effect separation of the portion 4 from the element 5. In the known arrangement, the continuation portion also carries the attachment material 15 as shown in FIG. 2.

With the existing product as described above, the attachment of the dependant portion 4, and thus of the first element 1, to the second element 5 is relatively firm, not only in the sense of resisting relative vertical opening forces, such as would be created by opening movements (voluntary or involuntary) of the eye lid, but also in the sense of resisting desired separation of the two elements 1 and 5 by deliberate withdrawal of the dependant portion 4 of element 1 from contact with the element 5, and thus from the patient's cheek, by pulling the tab 6. This can result in the unintended removal of the element 5 from the patient's cheek, and the likelihood of this occurrence can be increased by the siting of the element 5. If it is sited at a location which encourages the pulling apart of the portion 4 and the element 5 in a direction approximately at right angles to the cheek, the tendency towards removal of the element 5 is increased.

This invention aims at retaining reliable resistance to separation of the two elements by natural movements, or attempted movements, of the eye lid, whilst enhancing the ease of separation of the portion 4 from the element 5 when it is desired to pull them apart by means of the tab 6, in order to allow the eye to open, and a number of exemplary embodiments of the invention will now be described with reference to FIGS. 3 to 8.

Figure 3:
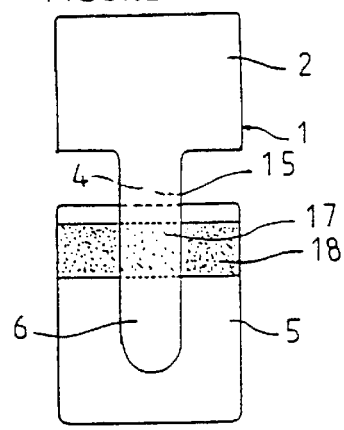
FIG. 3 shows, in plan view, an eye protector in accordance with a preferred embodiment of the invention.

FIG. 3 shows, in plan view, a preferred embodiment of the invention. The first element 1 comprises a generally rectangular pad portion 2, intended to be secured to the patient's eyelid as described hereinbefore. Depending from the pad portion 2, and integrally formed therewith, is a strip-like dependent portion 4 which extends downwardly, across the patient's eye in use, and bears retentive means 17 on its underside as viewed in the drawing. The strip-like portion 4 is configured to overlie co-operative retentive means 18 carried by the second element 5, which also is constituted by a rectangular pad. The arrangement is such that the area of overlap between the retentive means 17 borne by said strip-like portion 4 and that (18) carried by the second element 5 is relatively small compared with the area of the second element 5 as affixed to the patient's cheek.

In a particularly favoured arrangement, the second element 5 carries a strip 18 of said retentive material, said strip 18 extending, in use, substantially orthogonally to direction in which the said strip-like portion 4 depends from the pad portion 2 of said first element 1.

In one practical configuration, the dimensions of the pad portion 2 of the first element 1 are approximately 2.5 cm in width (measured transverse to the direction in which the strip-like portion 4 extends) and 2.0 cm in the orthogonal (depth) dimension. The strip-like portion is of width 0.9 cm and depth 3.5 cm (measured to its junction with the pad portion 2). The pad portion 5 is 2.5 cm in width and 3.3 cm in depth (using the same convention as above for these dimensions) and the retentive strip is 1 cm in depth, being disposed 0.2 cm from that surface of the pad 5 which is intended in use to be uppermost (i.e. closest to the bottom of the patient's eye.

The foregoing dimensions, whilst not intended to be limiting on the scope of the invention, have been found to work well in practice, providing firm anchorage of the two pad portions 2 and 5 on the one hand, whilst permitting ready separation of the two elements when required. It will be observed in this instance that the total area of the pad 5 of the second element is 2.5×3.3=8.25 square cm, whereas the area of overlap between the strip-like portion 4 and the strip 18 of retentive material provided on the pad 5 is 0.9×1.0 =0.9 square cm. The ratio between these areas is thus in excess of 9.1:1. Whilst this represents a preferred ratio, any ratio in excess of 2.5:1 though preferably in excess of 5:1 can be used to advantage.

Figure 4:
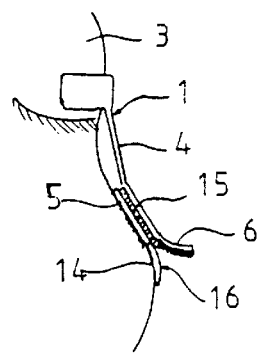
FIG. 4 shows, in profile view, the placement of an element upon the cheek of a patient which is usable by itself or in combination with other embodiments of the invention to facilitate separation of the two elements of an eye protector in accordance with the invention.

As shown in FIG. 4, a second embodiment of the eye protector of the present invention, which may be used alternatively to or in combination with the first embodiment, includes first and second elements 1 and 5 for respective attachment to the patient's eyelid 3 and cheek. Of note, in this embodiment, is that the second element 5 is arranged to be located so that it overlaps the lower part of the patient's eye socket. In particular, the second element 5 is extended so that it can be anchored in position with adhesive 14 around the lower edge of the patient's eye socket. As shown, the fastener means 15 provided to the second element does not extend beyond the edge of the eye socket. So as to facilitate the correct positioning of the second element on the Patient's cheek, an alignment means 16 may be present, such as a marking or indentation in the second element.

Further, the tab 6 of the first element is specifically not provided with fastener means.

With the embodiment of FIG. 4, the second element is anchored in such a position that in combination with the location of fastener means on the first and second elements works to resist release of the fastener means in response to natural eye lid motion but to release the fastener means more readily when manually pulled apart for detachment.

In the embodiments of FIGS. 5 to 8, material such as that sold under the Trade Mark VELCRO is applied to part only of one or both such surfaces and in an orientation, pattern or alignment that permits of progressive release of the portion 4 from the element 5 when pulled apart by means of the tab 6.

Figure 5:
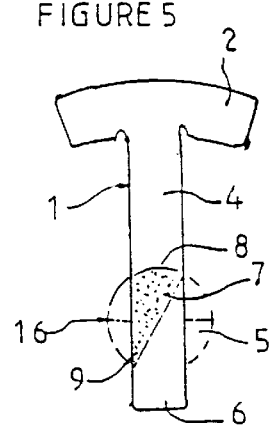
FIGS. 5 and 6 show, in plan view, different patterns of retentive material applied to the first element of a protector in accordance with another example of the invention.

FIG. 5 shows a pattern 7 of VELCRO (Trade Mark) material applied to the inner-facing surface of the strip-like portion 4 of element 1, and designed to achieve the intended resistance to opening by eye lid movement whilst permitting ready release of the element 1 from element 5 by pulling on tab 6. It will be observed that the pattern has a linear slant such as to present, at its upper region 8, a full width of the material to resist opening by eye lid motion but to present at its lower region 9 a much reduced width of the material which gradually increases towards the upper region 8, thereby permitting the elements 1 and 5 to be separated easily by pulling on the tab 6, initially with minimal force. The force required to pull the elements apart increases progressively as the removal proceeds, and it is found that this arrangement provides a marked reduction in the unwanted tendency to removal of the element 5.

Figure 6:
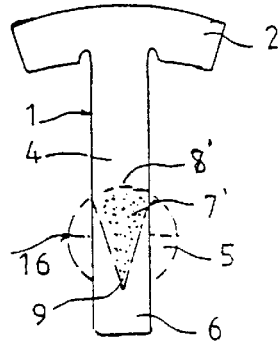

An alternative pattern is shown at 7' in FIG. 6, and other patterns achieving the desired effect will be evident to those skilled in the art. In particular, instead of conforming to a pattern exhibiting a substantially linear (or compound linear, e.g. stepped) width reduction as shown, the material may conform to a pattern exhibiting a more complex width reduction, such as exponential, logarithmic or sinusoidal.

It will be appreciated that the patterns of material shown as applied to the portion 4 in FIGS. 5 and 6 (or alternative patterns as aforesaid) could instead, or in addition, be applied to the element 5.

Figure 7:
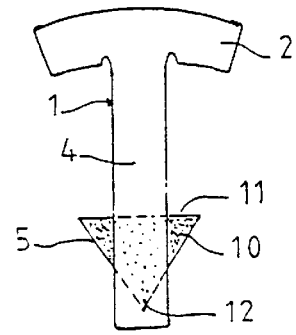
FIG. 7 shows, in plan view, a shaped second element of a protector in accordance with another example of the invention.
Figure 8:
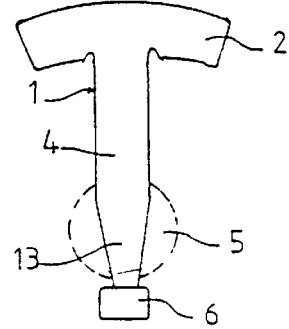
FIG. 8 shows, in plan view, a shaped first element of a protector in accordance with a still further example of the invention.

As a further alternative or additional expedient, the shape of the element 5 itself can be configured so as to achieve or enhance the desired result. In one example, as shown in FIG. 7, the element 5 is configured into a triangular shape 10, intended to be attached to the patient's cheek with the base 11 facing upwards, towards the patient's eye, and the apex 12 pointing downwards, away from the eyelid. Other shapes can of course be used for element 5 and, in particular, instead of conforming to a substantially triangular pattern with substantially linear sides, as shown, the shape may be more complex, with the base 11 preferably remaining substantially linear but the other sides conforming for example to stepped, exponential, logarithmic or sinusoidal configurations. Depending upon this shaping, the apex 12 may be characterised by an extremely sharp cusp or a more rounded shape. Moreover, whichever shape is adopted, the VELCRO (Trade Mark) material may completely cover the triangular or other shape, or may conform to the pattern shown in either FIG. 5 or FIG. 6, or another pattern as aforesaid. In FIG. 7, the outline of the element 1 is shown in phantom for convenience, and it will be appreciated that the triangular element 5 need not be as large as shown, in relation to the element 1. However there are constraints of convenience of handling and application to be borne in mind, and it is preferred to use elements of reasonable size to facilitate this, as well as to address general considerations such as the provision of a sufficient area of adhesive to ensure reliable attachment to the patient's skin.

In another alternative arrangement, the portion 4 is necked, as shown at 13 in FIG. 8, and in this case again the necked region 13 may be fully covered with the VELCRO (Trade Mark) material as shown or the material may be applied in a pattern such as that shown in FIG. 5 or FIG. 6, or another pattern as aforesaid.

The expedients described above in relation to FIGS. 3 or 5–8 may each be enhanced by dimensioning and configuring the elements 1 and 5 so that the element 5 can be attached to the patient's cheek in a position overlapping the eye socket as shown in FIG. 4. Moreover, the expedients involving patterning of the retentive material carried by elements 1 and/or 5, and/or shaping of the portion 4, can be used in combination with the FIG. 3 embodiment if desired.

Figure 9:
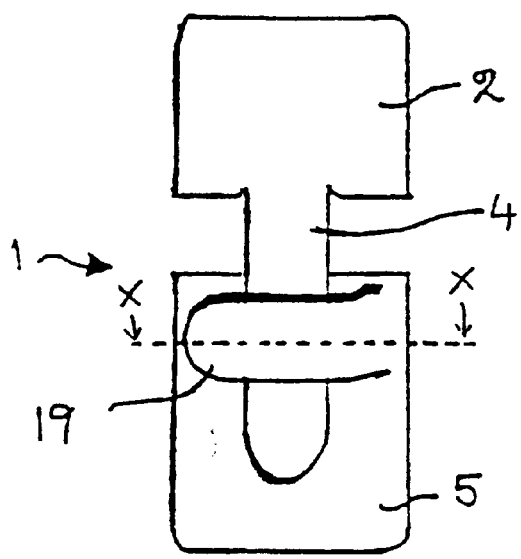
FIG. 9 shows, in plan view, a further example of a protector in accordance with the invention.
Figure 10:
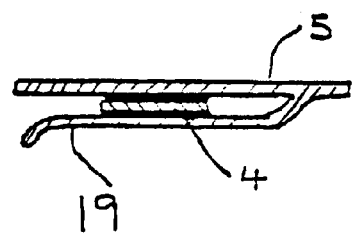
FIG. 10 shows a view on arrows X—X of FIG. 9.

In a further embodiment, shown in FIGS. 9 and 10, the second element 5 carries a laterally extending flap 19 which can be raised at its left-hand side (as viewed in FIG. 9) to permit the insertion thereunder of the downwardly dependent strip 4 of the first element 1. The strip 4 may be retained in place either by resilience of the material of the flap 19, which thus acts like a clip, in which case the flap 4 is preferably pre-formed as shown in FIG. 10 to assert the necessary retaining pressure on the dependent strip 4. In this regard, the flap 19 may, as shown, be integrally formed with the second element 5. Alternatively, the flap 19 may be formed separately from the element 2 and be permanently attached thereto by means such as a rivet or by ultrasonic welding or other known attachment procedures, in which case the element 5 may conveniently be made of a relatively thick but compliant material capable of absorbing pressure that might otherwise be applied to the patient's face by the retention force exerted by the resilience of the flap 19.

Alternatively, or in addition, the retention of the strip 4 may be achieved by the general or selective application of material such as Velcro (trade mark) to overlying and facing surfaces of the flap 19 and the strip 4, to part at least of the outer surface of element 5 and of the inner surface of the strip 4, and/or to the facing surfaces of element 5 and strip 4.

What is claimed is:

1. An eye protector comprising first and second elements intended for attachment respectively to a patient's upper eye lid and to a region of the patient's cheek beneath the eye to retain the eye lid in a fixed or closed position, and fastener means for releasably fastening the elements together, said fastener means comprising co-operatively retentive material carried by surfaces of respective components forming at least a portion of each of said first and second elements and intended in use to assume an overlying and contacting relationship, the area of overlap of retentive material of the first and second elements at a lower region of an area of overlap being configured to be relatively small compared with the associated area of the second element as affixed to the patient's cheek, the first element having a "T" shaped configuration comprising an upper portion in direct attachment with the patient's upper eye lid and a strip-shaped dependent portion extending downwardly across the patient's eye and bearing said retentive means configured to overlie co-operative retentive means carried by the second element, said strip of retentive material on the second element extending in use substantially orthogonally to said strip-like portion depending from said first element.

2. A protector according to claim 1, wherein the ratio of the total area of said second element as affixed to the patient's cheek to that of said area of overlap between the retentive means borne by said strip-shaped portion and that carried by the second element is in excess of 2.5:1.

3. A protector according to claim 1, wherein the ratio of the total area of said second element as affixed to the patient's cheek to said area of overlap between the retentive means borne by said strip-like portion and the retentive means carried by the second element is in excess of 5:1.

4. A protector according to claim 1, wherein the ratio of the total area of said second element as affixed to the patient's cheek to said area of overlap between the retentive means borne by said strip-shaped portion and the retentive means carried by the second element is in excess of 9:1.

5. A protector according to claim 1, wherein said element intended for attachment to the patient's upper eye lid further comprises a tab portion at its end not provided with retentive material and intended to be manipulated to detach the two elements from one another.

6. A protector according to claim 1, wherein the retentive material carried by at least one of said overlying components conforms to a pattern which presents a relatively wide profile towards the patient's eye and a profile of reduced width away from the eye.

7. A protector according to claim 6, wherein said pattern links said relatively wide profile to said profile of reduced width by means of at least one substantially linear slant.

8. A protector according to claim 6, wherein said pattern links said relatively wide profile to said profile of reduced width by means of at least one outline conforming to one of an exponential, logarithmic or sinusoidal form.

9. A protector according to claim 1, wherein at least one of said first and second elements includes a component shaped to present a wider profile towards the patient's eye than away therefrom.

10. A protector according to claim 1, wherein the second element, intended for attachment to the patient's cheek, is configured and dimensioned for attachment to an area overlapping the eye socket of the patient.

11. A protector according to claim 10, wherein the second element comprises alignment means for facilitating positioning thereof on the patient's cheek in use.

12. A protector according to claim 1, wherein the fastener means provided to the second element extends only on an upper portion of the second element.

13. An eye protector according to claim 1, wherein said first element comprises a downwardly dependent strip dimensioned so that a portion thereof overlies a part of said second element and said second element bears a laterally extending flap portion having one end thereof raisable to accommodate insertion of said strip and arranged in use to overlie said strip and to at least assist in retaining the strip in a location holding the patient's eye closed.

14. An eye protector according to claim 13, wherein said flap portion is integrally formed with said second element.

15. An eye protector according to claim 13, wherein said flap portion is formed separately from said second element and is attached thereto by fixing means.

* * * * *

UNITED STATES PATENT AND TRADEMARK OFFICE
CERTIFICATE OF CORRECTION

PATENT NO. : 6,764,459 B1
DATED : July 20, 2004
INVENTOR(S) : William Blair MacGregor Donaldson It is certified that error appears in the above-identified patent and that said Letters Patent is hereby corrected as shown below:

Title page,
Item [73], Assignee, should read as follows:
-- Bid Instruments Limited
  45 Carlton Place
  Aberdeen AB15 4BR
  Great Britain --.

Signed and Sealed this

First Day of November, 2005

JON W. DUDAS
*Director of the United States Patent and Trademark Office*